United States Patent [19]

Uchida et al.

[11] Patent Number: 5,283,181

[45] Date of Patent: Feb. 1, 1994

[54] CONJUGATED ENZYME ELECTRODE

[75] Inventors: Isamu Uchida; Tomokazu Matsue; Hsien-Chang Chang; Akinori Ueno; Hiroshi Yamada, all of Miyagi, Japan

[73] Assignee: Unitika, Ltd., Hyogo, Japan

[21] Appl. No.: 672,238

[22] Filed: Mar. 20, 1991

[30] Foreign Application Priority Data

Sep. 17, 1990 [JP] Japan .................................. 2-248025

[51] Int. Cl.$^5$ .......................... C12Q 1/32; C12N 1/00
[52] U.S. Cl. ............................................ 435/26; 435/4; 435/90; 435/817; 435/832; 436/86
[58] Field of Search ....................... 435/26, 4, 90, 817, 435/832; 436/86

[56] References Cited

PUBLICATIONS

Chang et al, *Chemical Abstracts*, vol. 114, Reference No. 100054m, 1991 (Denki Kagaku oyobi Kogyo Butsuri Kagaku 1990, 58(12) 1211–12).
Matsue et al, *Chemical Abstracts*, vol. 112, Ref. No. 231678z, 1990 (Biochim. Biophys. Acta 1990, 1038 (1) 29–38).
Weng et al, *Biological Abstracts*, vol. 90(6)-AB-56, Ref. No. 58161, 1990 (Anal. Chem. Acta 233(1) 59–64, 1990).
Chang et al, *Chemical Abstracts*, vol. 115, Ref. No. 154075h, 1991 (Analyst (London) 1991, 116(8), 793–6).
Miki et al, *Chemical Abstracts*, vol. 111, Ref. No. 74075k, 1989 (Anal. Sci. 1989, 5(3), 269–74).

*Primary Examiner*—Michael G. Wityshyn
*Assistant Examiner*—Abdel A. Mohamed
*Attorney, Agent, or Firm*—Sughrue, Mion, Zinn, Macpeak & Seas

[57] ABSTRACT

A conjugated enzyme electrode comprising diaphorase and an amino-acid dehydrogenase immobilized on a conductive support by a polyfunctional aldehyde is disclosed, by which amino acids can be rapidly determined with high sensitivity.

7 Claims, 2 Drawing Sheets

CONJUGATED ENZYME ELECTRODE

FIELD OF THE INVENTION

The invention relates to a conjugated enzyme electrode with excellent durability which enables instantaneous determination of amino acids in a sample.

BACKGROUND OF THE INVENTION

In the fields of clinical examinations, food analyses etc., amino acid analysis is of ever-increasing necessity, and demands for rapidity, simplicity and high reliability have been growing accordingly. Under such circumstances, bioassays utilizing enzyme reactions have attracted attention in the art because of substrate specificity of the enzymes and speed of reaction. Enzymes have taken a major role in various methods of amino acid analysis. In the clinical field, because of limitations of sample size and analysis time, there has been a need to develop a biosensor for amino acid determination which achieves not only improved rapidity and simplicity but also economy by reducing the need for costly reagents. In the food industry, too, a biosensor for amino acid determination excellent in rapidity, simplicity and economy has been demanded for process control, quality control and also for taste analysis as certain amino acids such as glutamic acid and alanine are substances with desirable tastes.

Known biosensors for amino acid determination include (1) an enzyme electrode comprising an amino-acid oxidase immobilized on an oxygen electrode or a hydrogen peroxide electrode, as disclosed in *Analytical Chemistry*, 47, 1359 (1975); (2) an analyzer comprising an amino-acid oxidase combined with a mass analyzer for improving rapidity, as disclosed in JP-A-60-52765 (the term "JP-A" as used herein means an "unexamined published Japanese patent application"); and (3) an enzyme electrode comprising an amino-acid oxidase and an amino-acid dehydrogenase or an aminotransferase immobilized on an electrode for increasing sensitivity, as disclosed in JP-A-60-73354.

Attempts were also made on (4) an enzyme electrode for alanine determination using glutamate-pyruvate transaminase and pyruvate oxidase immobilized on an electrode, as disclosed in JP-A-62-162952 and (5) an enzyme electrode using glutamatepyruvate transaminase and glutamate oxidase, as disclosed in *Chemistry Express*, Vol. 5, p. 125 (1990).

Because all the above described enzyme electrodes (1) to (5) use an oxidase, they are, in principle, susceptible to influences of dissolved oxygen or reducing substances. With respect to rapidity, only electrode (2) has a rate of response of within 1 minute. With respect to sensitivity, only electrodes (3) and (5) have a detection concentration limit on the order of $\mu M$ or less. Thus, an enzyme electrode for practical use which satisfies rapidity, high sensitivity and substantially sufficient durability has not yet been developed.

SUMMARY OF THE INVENTION

An object of the present invention is to provide a conjugated enzyme electrode for amino acid determination which achieves rapid determinations with high sensitivity and excellent durability while being free from influences of dissolved oxygen or reducing substances.

The inventors have conducted intensive and extensive studies with the above object in mind and, as a result, found that an enzyme electrode comprising diaphorase and an amino-acid dehydrogenase immobilized with a polyfunctional aldehyde as a crosslinking agent on a conductive support is capable of quantitatively determining presence of an amino acid with striking rapidity and high sensitivity and with an extended shelf life.

The present invention relates to a conjugated enzyme electrode comprising diaphorase and an amino-acid dehydrogenase immobilized on a conductive support by a polyfunctional aldehyde.

DETAILED DESCRIPTION OF THE INVENTION

Figure 1:
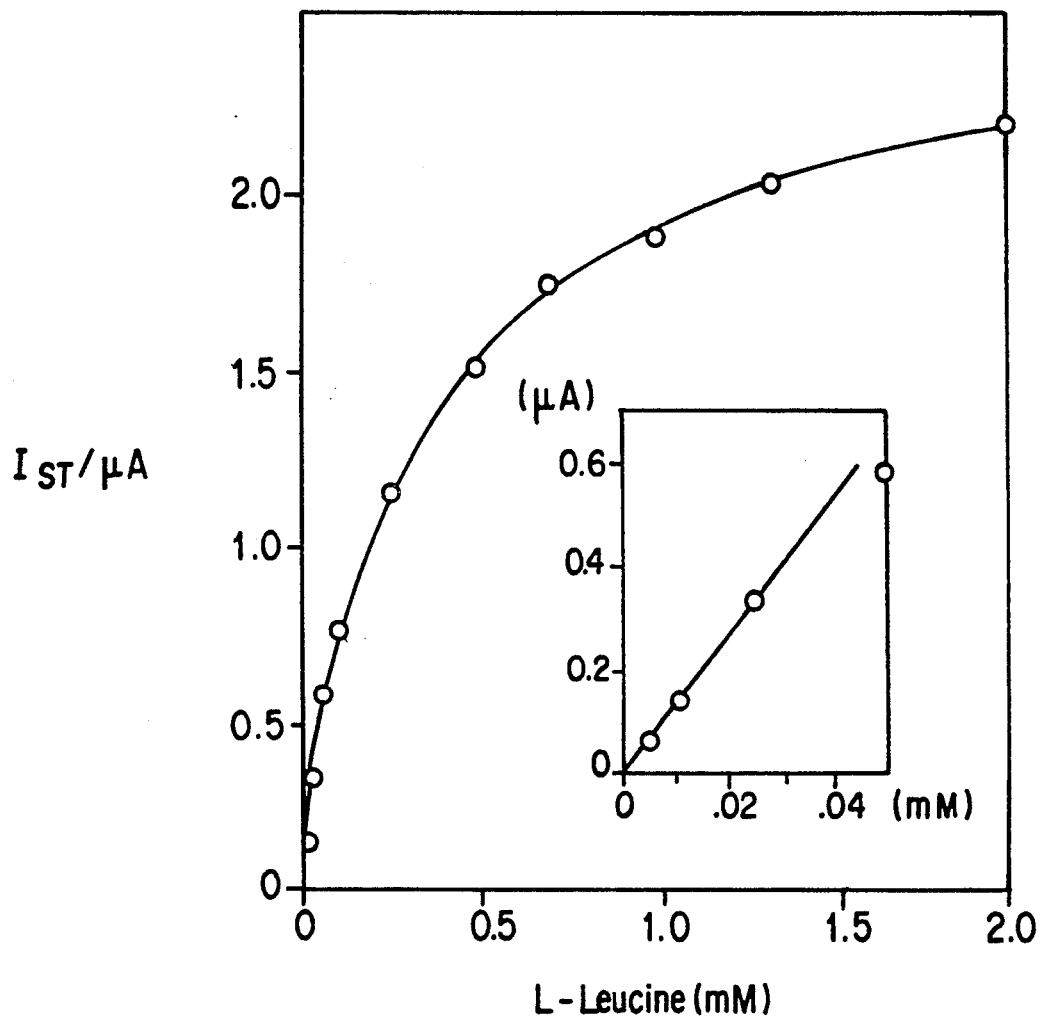
FIG. 1 is a graph showing the relationship between stationary current ($I_{st}$) or steady-state current of a buffer solution containing nicotinamide adenine dinucleotide and ferrocenyl methyl alcohol with an applied voltage of 0.2 V and varying concentrations of leucine.

The conductive support which can be used as an anode in the present invention includes gold electrodes, platinum electrodes and carbon electrodes, preferably carbon electrodes such as a graphite electrode, a carbon taste electrode and a glassy carbon electrode. A glassy carbon electrode is most advantageous. Cathodes which can be used in the determination include various electrodes, e.g., a platinum electrode, a carbon electrode, a gold electrode, a palladium electrode and a silver electrode. Reference electrodes for potential determination include a silver/silver chloride electrode and a saturated calomel electrode. A cathode and a reference electrode may be integrated into one body by using a palladium electrode, a silver electrode, a silver/silver chloride electrode, a saturated calomel electrode etc.

The diaphorase that can be used in the present invention includes various species originating in microorganisms or animals. Preferred are those enzymes of thermophilic bacteria with an optimum growth temperature of from 50° to 85° C., for example, microorganisms belonging to the genus Bacillus (e.g., *Bacillus stearothermophilus, Bacillus thermoproteolyticus* and *Bacillus acidocaldarius*), the genus Thermoactinomyces, the genus Thermus and the genus Thermomicrobium. *Bacillus stearothermophilus* is the most preferred. Specific examples of useful strains of *Bacillus stearothermophilus* are ATCC 7933, ATCC 7954, ATCC 10194, ATCC 12980, NCA 1503 (ATCC 29609), and UK 563 (Ferm P-7275).

The amino-acid dehydrogenase that can be used in the present invention includes various enzymes originating in microorganisms and animals. Preferred are those of thermophilic bacteria having an optimum growth temperature of from 50° to 85° C. Examples of such thermophilic bacteria are the same as those enumerated above. Those produced by microorganisms belong to the genus Leuconostoc or yeasts are also preferred.

Each of the diaphorase and the amino acid dehydrogenase can be obtained from the organisms according to known purification methods described, for example, in Robert K. Scopes, *Purification-Principles and Practice*, Springer-Verlag, N.Y. (1982). To separate and purify the enzymes, a solution containing a microorganism culture, an animal cell culture or animal-tissue, being smashed, is centrifuged, and then the resulted supernatant is subjected to a separation column generally used for enzyme purification, such as an ion-exchange column chromatography, a hydrophobic column chromatography, an affinity column chromatography and a gel column chromatography, to obtain the enzyme preparation with suitable purity. Some of the enzymes are also commercially available.

Each of the diaphorase and the amino acid dehydrogenase may be used at an arbitrary concentration. In a preferred embodiment, a solution of each enzyme in a concentration of from 0.1 to 30% by weight, and more preferably from 0.5 to 20% by weight, is applied to a conductive support in an amount of from 1 to 200 g/m$^2$, preferably from 1 to 150 g/m$^2$, more preferably from 1 to 120 g/m$^2$.

The polyfunctional aldehyde that can be used as a crosslinking agent includes bifunctional aldehydes such as glutaraldehyde, succinic aldehyde and glyoxal, and preferably glutaraldehyde. It is used as a solution in a concentration of from 0.1 to 10% by weight, and preferably from 0.5 to 3% by weight, and dropped on a conductive support in an amount of from 0.1 to 3 g/m$^2$.

Immobilization of diaphorase and an amino-acid dehydrogenase on a conductive support by a polyfunctional aldehyde crosslinking agent can be carried out by dropping solutions of the three components on a support either separately or in any combination thereof. In a preferred embodiment, a solution of a polyfunctional aldehyde is dropped lastly and the three solutions are uniformly mixed on the support.

Amino acid determinations using the enzyme electrode of the present invention can be conducted, for example, by dipping the electrode in a buffer solution containing nicotinamide adenine dinucleotide (hereinafter abbreviated as NADH) or nicotinamide adenine dinucleotide phosphate (hereinafter abbreviated as NADPH), which is a substrate for an amino-acid dehydrogenase, and a diaphorase mediator and measuring the stationary current of an electrode current generated on addition of a sample under analysis.

As a buffer solution, a 0.01 to 0.5M sodium phosphate buffer solution at a pH of from 5 to 10, and preferably from 7 to 9, is usually employed. The measurement temperature is from 0° to 60° C., and preferably from 20° to 40° C.

Mediators of diaphorase include ferrocene, ferrocene derivatives, N,N,N',N'-tetramethylphenylenediamine, 2,6-dichlorophenolindophenol, p-iodonitrotetrazolium violet, nitro blue tetrazolium, quinone compounds, e.g., vitamin K, and cytochrome c, with ferrocenylmethanol and ferrocenyl-1-ethanol being preferred.

In the above-described analysis system, the conjugated enzyme electrode according to the present invention enabled a determination with striking rapidity requiring a response time of about 30 seconds.

Besides excellence in rapidity, the enzyme electrode of the present invention exhibited excellent durability, that is retaining performance for more than half a year without any means commonly employed for stabilization of an immobilized enzyme membrane, such as covering with a selective permeable membrane, e.g., cellulose membranes (e.g., cellulose acetate and nitrocellulose), or various natural or synthetic high polymer membranes.

Using the enzyme electrode according to the present invention, it is possible to produce a flow injection type analyzer, by which system automating and shorter analysis time would be achieved.

The simple structure of the enzyme electrode of the present invention makes it possible to prepare various microelectrodes for amino acid determination by selecting an amino-acid dehydrogenase specific to each amino acid to be determined, thereby permitting a reduction in the requisite amount of a sample to be analyzed and broadening of the application to microsamples.

The present invention is now illustrated in greater detail with reference to Examples, but it should be understood that the present invention is not limited thereto. All the percents are by weight unless otherwise indicated.

EXAMPLE 1

Preparation of Electrode:

A glassy carbon disc having a diameter of 3 mm ("GC-20" produced by Tokai Carbon K.K.) was polished with sand paper and alumina abrasive grains having a particle size of 0.05 μm and then washed with distilled water in a ultrasonic cleaner. On the thus polished surface were dropped 0.4 μl of a 60 mg/ml solution of *Bacillus stearothermophilus* diaphorase (produced by Unitika Ltd.) and 20 μl of a 14 mg/ml solution of *Bacillus stearothermophilus* leucine dehydrogenase (produced by Unitika Ltd.), which were then mixed together. Then, 0.5 μl of a 2% glutaraldehyde solution were dropped thereon by means of a microsyringe and mixed with the enzyme solution without delay. The mixed solution was freed of the solvent by allowing the support to stand at room temperature for one day to thereby prepare an immobilized enzyme membrane.

The resulting enzyme electrode was preserved in a 0.05M phosphoric acid buffer solution (pH=7.5) at 4° C. before use.

Electrochemical Measurement:

The enzyme electrode, a potentiostat ("HAB-151" produced by Hokuto Denki K.K.), and an X-Y recorder ("WX 43096" produced by Graphtec Co.) were assembled into a three-electrode system. A 0.05M phosphoric acid buffer solution (pH=7.5) was used as a basal solution. A magnetic stirrer was set about 1 mm under the electrode to agitate the solution at a rate of 800 rpm or more. The electrode potential was measured using a silver/silver chloride electrode as a standard at a temperature controlled at 30° C.

Determination of Leucine:

The above prepared glassy carbon electrode having immobilized thereon diaphorase and leucine dehydrogenase was immersed in a 50 mM phosphoric acid buffer solution (pH=7.5) containing 0.5 mM NADH and 0.1 mM ferrocenyl methyl alcohol, and the electrode potential was fixed at 0.2 V. Leucine was added to the buffer solution and, after a steady state was reached (within about 30 seconds), an oxidation current was measured.

Dependence of the oxidation current on leucine concentration under the stationary state ($I_{st}$) (corrected for a residual current) is shown in FIG. 1. FIG. 1 is a graph showing the relationship between the stationary current $I_{st}$ in a buffer solution containing NADH and ferrocenyl methyl alcohol as a mediator of diaphorase, with an applied voltage of 0.2 V (ordinate) and the leucine concentration in the sample (abscissa). As is apparent from FIG. 1, the stationary current $I_{st}$ shows good linearity up to a leucine concentration of 50 μM, and the detection limit was 2 μM.

Figure 2:
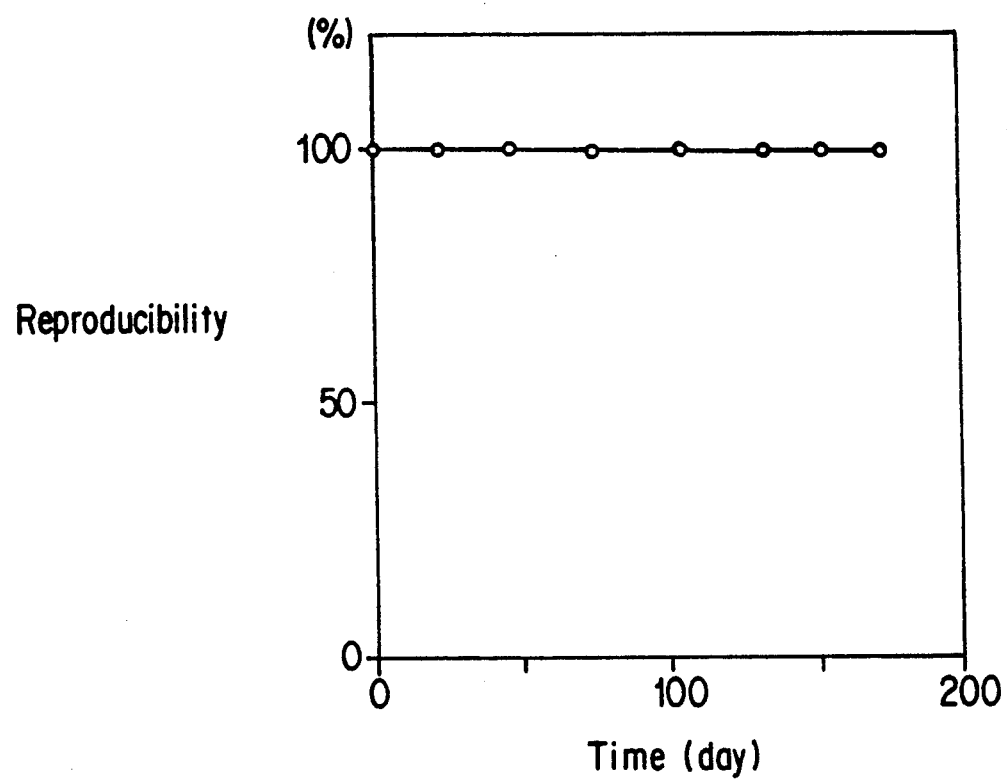
FIG. 2 is a graph showing reproducibility and durability of the conjugated enzyme electrode according to the present invention.

FIG. 2 shows reproducibility when a sample containing leucine at a concentration of 50 μM was analyzed 110 times over 170 days. The coefficient of variation was within 5% proving the enzyme electrode of the present invention is markedly excellent in reproducibility and durability.

EXAMPLE 2

Leucine in human urine was determined, without any pretreatments to the sample, by using the conjugate enzyme electrode for leucine determination as prepared in Example 1. The result obtained is shown in Table 1 below. The result agreed very closely with that obtained by conventional spectroscopic analysis using leucine dehydrogenase which is also shown in Table 1.

TABLE 1

| Method of Analysis | Measured Value |
| --- | --- |
| Method of Invention | 40 μM |
| Spectroscopic Analysis | 34 μM |

EXAMPLE 3

On the same polished glassy carbon disk as used in Example 1 were dropped 0.9 μl of a 60 mg/ml solution of *Bacillus stearothermophilus* diaphorase (produced by Unitika Ltd.) and 20 μl of a 20 mg/ml solution of bovine liver glutamate dehydrogenase (produced by Oriental Yeast K.K.) and the solutions were mixed. Then 0.5 μl of a 1% glutalaldehyde solution were dropped by means of a microsyringe. The mixed solution was treated in the same manner as in Example 1 to prepare an enzyme electrode for glutamic acid determination.

Glutamic acid in soy sauce was determined, without any pretreatments to the sample, in the same manner as in Example 1 using the above prepared electrode (measurement time: within 30 seconds). The result obtained is shown in Table 2 below. For comparison, the result obtained by using an amino acid analyzer ("Hitachi Amino Acid Analyzer") is also shown. Both results showed good agreement with each other.

TABLE 2

| Method of Analysis | Measured Value |
| --- | --- |
| Method of Invention | 123 mM |
| Amino Acid Analyzer | 128 mM |

While the invention has been described in detail and with reference to specific examples thereof, it will be apparent to one skilled in the art that various changes and modifications can be made therein without departing from the spirit and scope thereof.

What is claimed is:

1. A conjugated enzyme electrode for amino acid determination comprising diaphorase and an amino-acid dehydrogenase immobilized on a conductive support through crosslinking with a polyfunctional aldehyde.

2. The conjugated enzyme electrode of claim 1, wherein said diaphorase is produced by a microorganism whose optimum growth temperature is from 50° to 80° C.

3. The conjugated enzyme electrode of claim 1, wherein said diaphorase and amino-acid dehydrogenase is each produced by a microorganism whose optimum growth temperature is from 50° to 85° C.

4. The conjugated enzyme electrode of claim 1, wherein said polyfunctional aldehyde is glutaraldehyde.

5. A method of determining concentration of an amino acid in a sample comprising the steps of:
 (a) placing an electrode of claim 1 into a buffer solution comprising an amino acid dehydrogenase substrate and a diaphorase mediator wherein said mediator accepts electrons from said diaphorase and donates said electrons to said electrode;
 (b) adding said sample to said buffer solution;
 (c) measuring a stationary or steady-state current at said electrode generated on addition of said sample to said buffer solution; and
 (d) determining said concentration by correlating the measured current to a standard.

6. The method of claim 5, wherein said amino acid dehydrogenase substrate is nicotinamide adenine dinucleotide or nicotinamide adenine dinucleotide phosphate.

7. The method of claim 5, wherein said diaphorase mediator is ferrocenylmethanol or ferrocenyl-1-ethanol.

* * * * *